United States Patent [19]
Diamond et al.

[11] B 3,996,232
[45] Dec. 7, 1976

[54] 1,5-DISUBSTITUTED BIGUANIDES

[75] Inventors: Julius Diamond, Morris Plains, N.J.; Bernard J. Burns, Philadelphia, Pa.

[73] Assignee: William H. Rorer, Inc., Fort Washington, Pa.

[22] Filed: Oct. 3, 1973

[21] Appl. No.: 403,243

[44] Published under the second Trial Voluntary Protest Program on March 30, 1976 as document No. B 403,243.

Related U.S. Application Data

[63] Continuation of Ser. No. 92,256, Nov. 23, 1970, abandoned.

[52] U.S. Cl. .................. 260/293.79; 260/293.78; 260/471 R; 260/471 A; 260/479 R; 260/479 S; 260/518 R; 260/518 A; 260/556 AR; 260/556 B; 260/564 B; 260/565; 424/267; 424/326

[51] Int. Cl.² ..................................... C07D 295/14

[58] Field of Search ............... 260/293.78, 293.79, 260/471 R, 471 A, 479 R, 479 S, 518 R, 518 A, 556 AR, 556 B, 564 B, 565

[56] References Cited
UNITED STATES PATENTS

| 2,467,371 | 4/1949 | Curd et al. | 260/565 |
|---|---|---|---|
| 2,510,081 | 6/1950 | Curd et al. | 260/565 |
| 2,544,827 | 3/1951 | Curd et al. | 260/565 |
| 2,934,535 | 4/1960 | Sutton | 260/249.9 |
| 3,119,867 | 1/1964 | Lecher et al. | 260/553 |
| 3,222,398 | 12/1965 | Brown | 260/565 |
| 3,456,059 | 7/1969 | Wick et al. | 424/326 |
| 3,553,263 | 1/1971 | Rosenwald et al. | 260/565 |

OTHER PUBLICATIONS

Yale, J. Med. Chem. 1(2), 121 (1959).
Burn et al., Brit. J. Pharmacol. 3, 346–351 (1948).

Primary Examiner—G. Thomas Todd
Attorney, Agent, or Firm—James A. Nicholson

[57] ABSTRACT

Novel 1-aryl and aralkyl 5-substituted biguanide compounds have been prepared. The compounds of this invention possess useful antiulcerogenic properties.

21 Claims, No Drawings

1,5-DISUBSTITUTED BIGUANIDES

CROSS REFERENCE TO RELATED APPLICATIONS

This is a continuation of application Ser. No. 92,256 filed Nov. 23, 1970, now abandoned.

SUMMARY OF THE INVENTION

This invention describes new 1,5-disubstituted biguanide compounds and processes for their preparation. This invention further provides valuable pharmaceutical preparations which contain 1,5-disubstituted biguanide compounds as active antiulcerogenic agents. The process for their preparation is also described.

BACKGROUND OF THE INVENTION

The pharmaceutical compositions which have been used as antiulcerogenic agents have been such as atropine, homatropine, propantheline bromide, dicyclomine hydrochloride and other compounds which are structurally dissimilar to the biguanides of this invention. Due to the anticholinergic properties of these compounds they are known to produce undesirable side effects such as mydriasis, xerostomia, cyclopegia and other unwanted effects.

There have been a number of 1-aryl and arlkyl-5-i-propylbiguanides described in the literature. They have been proposed for use as antimalarial agents. These findings, however, have not shown any antiulcerogenic effects have been associated with these compounds.

We have found novel 1,5-disubstituted biguanides are valuable pharmacologic agents possessing useful anti-secretory, anti-spasmodic and anti-ulcerogenic properties.

We have also found that the compounds of this invention are substantially free of the anticholinergic side-effects which accompany antiulcerogenic agents.

We have further found a simple and effective method for treating duodenal and peptic ulcers.

We have found that the 1,5-disubstituted biguanides of this invention are conveniently prepared.

We have also found that the instant compounds possess mucogenic properties.

DESCRIPTION AND PREFERRED EMBODIMENT

This invention describes a class of novel chemical compounds which contain a 1-phenyl, substituted phenyl, aralkyl or substituted aralkyl radical attached to a 5-substituted biguanide chain. This invention further describes its non-toxic pharmaceutically acceptable salts and the method of preparing the instant compounds.

The novel compounds of this invention are generically described by the structural formula I:

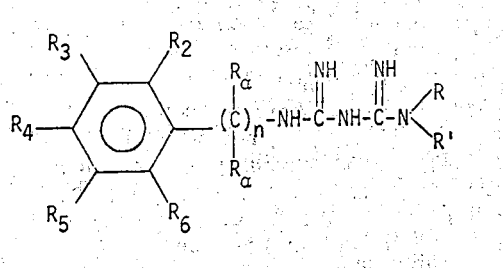

where:
$n$ is 0–1;
R is hydrogen or loweralkyl;

$R_2$, $R_3$, $R_4$, $R_5$ and $R_6$ may be the same or different and are
hydrogen (provided they are not all hydrogen at the same time),
haloloweralkyl,
hydroxy,
carboxy,
carbalkoxy,
diloweralkylsulfonamido
phenoxy,
halophenoxy,
acyloxy,
haloloweralkoxy,
thiocyanato,
phenyl,
halophenyl,
amino,
mono- and diloweralkylamino;
R and R' are
loweralkyl,
intermediate alkyl,
loweralkenyl,
cycloalkyl, cycloalkylloweralkyl,
aryl,
aralkyl,
cycloloweralkenyl or
hydrogen provided both R and R' are not hydrogen at the same time;
R and R' together are
loweralkylidenyl or
heteroloweralkylidenyl;
$R_2$, $R_3$, $R_4$, $R_5$ and $R_6$ may also be
bromo,
fluoro,
iodo,
nitro,
loweralkyl,
loweralkylthio or
cyano provided at least one of $R_2$, $R_3$, $R_4$, $R_5$ and $R_6$ are other than hydrogen;
$R_2$, $R_3$, $R_4$, $R_5$ and $R_6$ may also be
chloro provided R is other than lower alkyl or fewer than three hydrogen atoms are present when chloro is the only substituent and that $R_3$, $R_4$ and $R_5$ are not all chloro at the same time; and their non-toxic acid addition salts.

The more preferred compounds of this invention embrace those compounds of structural formula II:

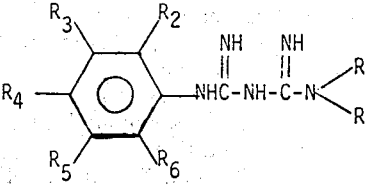

where:
$R_2$, $R_3$, $R_4$, $R_5$ and $R_6$ are
hydrogen (provided they are not all hydrogen at the same time), or
haloloweralkyl;
R and R' are
loweralkyl,
intermediatealkyl,
cycloalkyl or
hydrogen provided both R and R' are not hydrogen at the same time;

$R_2$, $R_3$, $R_4$, $R_5$ and $R_6$ may be
  fluoro,
  bromo,
  iodo or
  nitro provided $R_2$ and $R_6$ are not both hydrogen at the same time, or chloro provided R is other than loweralkyl or fewer than three hydrogen atoms are present when chloro is the only substituent and that $R_3$, $R_4$, $R_5$ are not all chloro at the same time.

The most preferred compounds of this invention are described by structural formula II:
where:
  $R_2$, $R_3$, $R_4$, $R_5$ and $R_6$ are
    hydrogen (provided thay are not all hydrogen at the same time) or
    trifluoromethyl;
  R and R' are
    loweralkyl,
    intermediate alkyl or
    hydrogen provided both R and R' are not hydrogen at the same time;
  $R_2$, $R_3$, $R_4$, $R_5$ and $R_6$ may be
    fluoro,
    bromo, or
    nitro provided $R_2$ and $R_6$ are not both Hydrogen at the same time or chloro when R is other than loweralkyl or fewer than three hydrogen atoms are present when chloro is the only substituent and that $R_3$, $R_4$ and $R_5$ are not all chloro at the same time.

In the descriptive portions of this invention, the following definitions apply:

The term "lower alkyl" refers to an alkyl hydrocarbon group containing from 1 to 5 carbon atoms which may be straight chained or branched.

The term "intermediate alkyl" refers to an alkyl hydrocarbon group containing from 6 to 12 carbon atoms which may be straight chained or branched.

The "acyl" radical may be any organic radical derived from an organic acid by its removal of the hydroxyl group such as acetyl, propionyl, benzoyl, etc.

The "lower alkoxy" radical signifies an alkoxy group containing from 1 to about 6 carbon atoms which can be straight chained or branched.

The "loweralkenyl" group refer to an alkenyl hydrocarbon group containing from 2 to about 6 carbon atoms which may be straight chained or branched.

"Cycloalkyl" refers to a cycloalkyl hydrocarbon ring having from 3 to 8 carbon atoms.

"Cycloalkenyl" refers to a cycloalkenyl hydrocarbon ring having from 3 to 8 atoms.

The "loweralkylidenyl" radical refers to an alkylidene hydrocarbon radical containing from 2 to 6 carbon atoms thus forming a ring.

The "heteroloweralkylidenyl" radical refers to an alkylidene hydrocarbon radical containing from 2 to 6 carbon atoms and one or more hetero atoms selected from oxygen, nitrogen and sulfur, thus forming a hetero ring. "Aryl" refers to an aromatic ring preferably phenyl.

It is well known in the pharmacological arts that non-toxic acid addition salts of pharmacologically active amine compounds do not differ in activities from their free base. The salts merely provide a convenient solubility factor. The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid, etc. |

It will further be appreciated by one skilled in the art that the following radicals may be employed in the practice of this invention:
where:
  $n$ is also 2;
  R is
    loweralkenyl,
    cycloloweralkyl,
    haloloweralkyl,
    arloweralkyl or
    aryl;
  $R_2$, $R_3$, $R_4$, $R_5$ and $R_6$ are
    loweralkenyl,
    aminoloweralkyl,
    alkylaminoloweralkyl,
    hydroxyloweralkyl,
    mercapto,
    loweralkylsulfinyl,
    loweralkylsulfonyl,
    sulfonamido,
    loweralkoxyloweralkyl,
    mercaptoloweralkyl,
    loweralkylmercaptoloweralkyl,
    arloweralkylmercaptoloweralkyl,
    arloweralkyl,
    arloweralkenyl,
    halobenzyl,
    anilino,
    loweralkoxyphenyl,
    biphenylyl,
    benzyloxy,
    a polyfluoro substituted group such as
    trifluoromethylsulfonyl,
    trifluoroacetyl,
    trifluoroacetoxy,
    trifluorocarbomethoxy,
    di-(trifluoromethylamino)sulfonyl,
    di-(trifluoromethylamino)carbonyl, or
    $\beta,\beta$-difluorovinyl.

The products of this invention can contain an asymetric carbon atom when $n=1$. For this reason they may be obtained as racemic mixtures or as dextro (+) and levorotatory (−) isomers. These may be separated by any of the various methods of resolution to obtain the pure $d$- or $l$- biguanide compound. It is to be understood that these optical isomers are embraced within the scope of this invention.

Representative compounds of this invention which are particularly useful are as follows:
  1(p-trifluoromethylphenyl)15-i-propylbiguanide
  1-(p-trifluoromethoxyphenyl)-5-i-propylbiguanide
  1-(p-dimethylsulfamylphenyl)-5-i-propylbiguanide
  1-(p-trifluoromethylbenzyl)-5-i-propylbiguanide
  1-(2,6-dibromophenyl)-5-methylbiguanide 1-(2,4,6-trichlorophenyl)-5-methylbiguanide
1-(2,4,6-tribromophenyl)-5-methylbiguanide
1-(2,6-dichlorobenzyl)-5-methylbiguanide
1-(2,6-dichloro-4-hydroxyphenyl)-5-methylbiguanide
1-(2,6-dichloro-4-bromophenyl)-5-methylbiguanide
1-(2,6-dichloro-α-methylbenzyl)-5-methylbiguanide
1-(3,5-ditrifluoromethylphenyl)-5-methylbiguanide
1-(3,4,5-trimethoxyphenyl)-5-methylbiguanide
1-(2,4,6-trimethoxyphenyl-5-methylbiguanide
1-(3,5-dichloro-4-methoxyphenyl)-5-methylbiguanide
1-(2,3,4,6-tetrafluorophenyl)-5-methylbiguanide
1-(2,3,4,5-tetrafluorophenyl)-5-methylbiguanide
1-(2,6-dibromo-4-trifluoromethylphenyl)-5-methylbiguanide
1-(2,6-dibromo-4-chlorophenyl)-5-methylbiguanide
1-(2,6-dichloro-4-trifluoromethylphenyl)-5-methylbiguanide
1-(2,4-dichloro-6-thiocyanatophenyl)-5-methylbiguanide
1-(2,6-dibromo-4-fluorophenyl)-5-methylbiguanide
1-(2,6-dibromo-4-iodophenyl)-5-methylbiguanide
1-(2,6-dichloro-4-nitrophenyl)-5-methylbiguanide
1-(2,6,4'-trichloro-4-biphenyl)-5-methylbiguanide
1-(2,6-dichloro-4-phenoxyphenyl)-5-methylbiguanide
1-(2,6,4'-tribromo-4-phenoxyphenyl)-5-methylbiguanide
1-(p-trifluoromethylphenyl)-5-methylbiguanide
1-(p-trifluoromethylphenyl)-5,5-dimethylbiguanide
1-(p-trifluoromethylphenyl)-5,5-methylethylbiguanide
1-(p-trifluoromethylphenyl)-5-cyclopropylbiguanide
1-(p-trifluoromethylphenyl)-5-heptylbiguanide
1-(p-trifluoromethylphenyl)-5-octylbiguanide
1-(p-trifluoromethylphenyl)-5,5-dioctylbiguanide
1-(p-trifluoromethylphenyl)-5-benzylbiguanide
1-(p-trifluoromethylphenyl)-5-phenylbiguanide
1-(4-nitro-2-trifluoromethylphenyl)-5-methylbiguanide
1-(3-nitro-4-trifluoromethylphenyl)-5-methylbiguanide
1-(2-nitro-4-trifluoromethylphenyl)-5-methylbiguanide
1-(4-fluoro-2-trifluoromethylphenyl)-5-methylbiguanide
1-(4-fluoro-3-trifluoromethylphenyl)-5-methylbiguanide
1-(2-fluoro-5-trifluoromethylphenyl)-5-methylbiguanide
1-(2-bromo-5-trifluoromethylphenyl)-5-methylbiguanide
1-(2-chloro-5-trifluoromethylphenyl)-5-methylbiguanide
1-(4-chloro-3-trifluoromethylphenyl)-5-methylbiguanide
1-(4-bromo-3-trifluoromethylphenyl)-5-methylbiguanide
1-(4-bromo-2-trifluoromethylphenyl)-5-methylbiguanide.

The compounds of this invention may be prepared by the following general procedures:

Condensation of substituted cyanoguanide and an aryl or aralkylamine in the presence of an equimolar amount of a mineral acid results in the corresponding aryl or aralkyl-5-substituted biguanide.

The following reaction equation illustrates this synthesis:

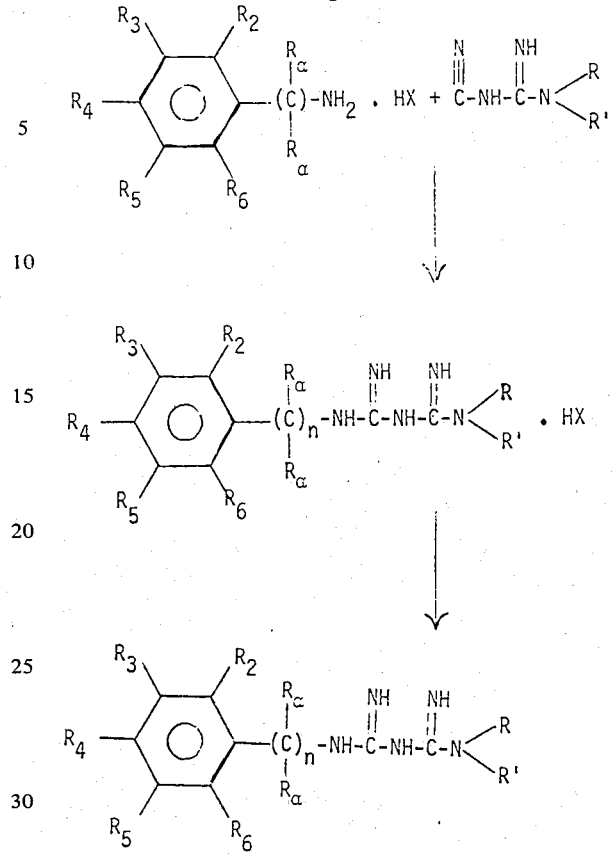

where $n$, $R_\alpha$, $R_2$, $R_3$, $R_4$, $R_5$, $R_6$, R and R' are as described above, and HX is a mineral acid.

The reaction is preferably carried out on the aryl or aralkylamine salt either in a polar medium or neat and using increased temperatures. The salt used may be any acid addition amine salt but preferably the salt of a mineral acid. The polar medium may be aqueous, partially aqueous or a non-aqueous solution. It is convenient to choose a solvent that will reflux at the desired reaction temperature. The more preferred solvents are water or alcohol but other solvents may be used such as DMSO, diethyleneglycol, ethyleneglycol, tetrahydrofuran, dimethylformamide, etc. The reaction should also be carried out at a temperature which is high enough so that condensation takes place readily, but not sufficient to decompose the biguanide formed. The reaction temperature can vary from room temperature to about 250°C although it is preferable to run the reaction at temperatures from about 50°C to 150°C. The biguanide salt which is formed can be converted to the free base with a metal hydroxide or alkoxide solution. The isolation of the desired biguanide can be carried out by any method known in the art.

Appropriately desired end products having various $R_2$, $R_3$, $R_4$, $R_5$ and $R_6$ substituents can be prepared at various stages of synthesis using suitable reactions in order to convert one group to another. Thus, for example, using conventional methods, a halogen group can be treated under Rosenmund Von Brown conditions to the nitrile compound which in turn can be hydrolyzed to a carboxy. A nitro can be reduced to an amino which can be alkylated to the dialkylamino substituent. A hydroxy compound can be prepared by demethylation of a methoxy substituent. A Sandmeyer type reaction can be carried out on an amino compound to introduce a chloro, bromo, xanthate, hydroxyl or alkoxyl group.

The xanthate can then lead to the mercapto by hydrolysis, this in turn can be alkylated to an alkylthio group which can be oxidized to alkylsulfinyl and alkylsulfonyl groups. A thiocyanato group may be reduced to a mercapto. An iodo group may be removed by catalytic hydrogenation. Reactions can also be carried out on 1-phenyl-5-substituted biguanide compounds which result in further substituted products. In this regard, we have found that 1-phenyl-5-substituted biguanides may be halogenated, nitrated or thiocyanated to obtain other and/or para substituted products. Thus, for example, bromination can be carried out on the following 1-phenyl-5-substituted biguanides to obtain the desired products:

1-(4-trifluoromethylphenyl)-5-i-propylbiguanide
1-(4-bromophenyl)-5-methylbiguanide
1-(4-fluorophenyl)-5-methylbiguanide
1-(4-chlorophenyl)-5-methylbiguanide
1-(2,6-dichlorophenyl)-5-methylbiguanide
1-(4-iodophenyl)-5-methylbiguanide
1-(4-nitrophenyl)-5-methylbiguanide
1-(4'-chloro-4-biphenyl)-5-methylbiguanide
1-(4-phenoxyphenyl)-5-methylbiguanide
1-[4-(4'-chlorophenoxy)phenyl]-5-methylbiguanide
1-(2,4-dichlorophenyl)-5-methylbiguanide 1-(2,6-dibromo-4-trifluoromethylphenyl)-5-i-propylbiguanide
1-(2,4,6-tribromophenyl)-5-methylbiguanide
1-(2,6-dibromo-4-fluorophenyl)-5-methylbiguanide
1-(2,6-dibromo-4-chlorophenyl)-5-methylbiguanide
1-(2,6-dichloro-4-bromophenyl)-5-methylbiguanide
1-(2,6-dibromo-4-iodophenyl)-5-methylbiguanide
1-(2,6-dibromo-4-nitrophenyl)-5-methylbiguanide
1-(2,6-dibromo-4'-chloro-4-biphenyl)-5-methylbiguanide
1-(2,6-dibromo-4-phenoxyphenyl)-5-methylbiguanide
1-[2,6-dibromo-4-(4'-chlorophenoxy)phenyl]-5-methylbiguanide
1-(2,4-dichloro-6-bromophenyl)-5-methylbiguanide In an analogous manner, chlorination, nitration and thiocyanation can also be carried out to obtain corresponding products. Other reactions known in the art may also be employed.

The starting materials of this invention are either known compounds or their method of preparation is described.

We have found that the compounds of this invention have useful antiulcerogenic properties. Further they have an effective degree of gastric anti-secretory activity and effectively reduce the volume and the acidity of the gastric fluid in humans and mammals. Still further, these compounds produce a considerable spasmolytic action on the gastrointestinal musculature, i.e., they reduce the peristaltic action of the gastrointestinal musculature which is manifested by a delay in gastric emptying time.

Until now, the known antiulcerogenic compounds which showed gastric anti-secretory and gastrointestinal spasmolytic action have included such agents as atropine, homatropine, propantheline, dicyclomine, etc. These compounds, however, cause accompanying undesirable anti-cholinergic properties such as mydriasis, xerostomia, cyclopegia, etc. We have found that the 1-aryl and aralkyl-5-substituted biguanides of this invention are particularly useful as anti-secretory, anti-spasmotic and anti-ulcerogenic agents because they are essentially devoid of these unwanted effects.

In particular the 1-aryl and aralkyl-5-substituted biguanides as herein described are useful in the treatment of such ulcerogenic disorders and diseases as duodenal ulcer and peptic ulcer.

The instant compounds may be used alone or in combination with other known antacids such as aluminum hydroxide, magnesium hydroxide, magnesium trisilicate, aluminum glycinate, calcium carbonate and the like.

For all these purposes, the 1,5-disubstituted biguanides of this invention can be normally administered orally or parenterally. Orally they may be administered as tablets, aqueous or oily suspension, dispersible powders or granules, emulsions, hard or soft capsules, or syrups or elixirs. The term parenteral as used herein, includes subcutaneous injection, intravenous, intramuscular or intrasternal injection or infusion techniques.

Compositions intended for oral use may be prepared according to any method known to the art for the manufacture of pharmaceutical compositions and such compositions may contain one or more agents selected from the group consisting of sweetening agents, flavoring agents, coloring agents and preserving agents, in order to provide a pharmaceutically elegant and palatable preparation.

Further, these compounds may be tableted or otherwise formulated so that for every 100 parts by weight of the composition, there are present between 5 and 95 parts by weight of the active ingredient. The dosage unit form will generally contain between about 1 mg. and about 500 mg. of the active ingredients of this invention. The preferred unit dose is between about 10 mg. and about 100 mg.

The dosage regimen in carrying out the methods of this invention is that which insures maximum therapeutic response until improvement is obtained and thereafter the minimum effective level which gives relief. Thus, in general, the dosages are those that are therapeutically effective in the treatment of ulcerogenic disease conditions or symptoms, such as duodenal and peptic ulcer. In general, the daily dose can be between about 0.1 mg/kg and 70 mg/kg (preferably in the range of 1–25 mg/kg/day), bearing in mind, of course, that in selecting the appropriate dosage in any specific case, consideration must be given to the patient's weight, general health, age and other factors which may influence response to the drug.

Various tests in animals have been carried out to show the ability of the compounds of this invention to exhibit reactions that can be correlated with anti-ulcerogenic activity in humans. These tests involve such as the effect of the 1-aryl and aralkyl-5-substituted biguanides on gastric secretion, gastro-intestinal spasm and their mucogenic effect. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compound or the vehicle immediately subsequent to the ligation of the stomach at the pyloric sphincter. The animals are sacrificed with chloroform at 4 hours post-drug administration, the stomach is removed and its contents are assayed for volume, pH and total acids.

A second gastric secretion test is carried out on dogs. This is outlined in the Handbook of Physiology, Section 6: Alimentary Canal, Volume II: Secretion, American Physiology Society, Washington, D.C., 1967.

It has been found that the compounds of this invention when subjected to the above gastric secretion tests display a marked ability to decrease gastric volume and gastric acidity. These tests are known to correlate well with gastric activity in humans and is a standard test used to determine anti-secretory properties.

To determine the anti-ulcer effectiveness the following test is employed: Male Wistar rats (130–150 grams) are fasted for 24 hours, then given reserpine at 5 mg/kg i.p. Twenty-four hours later, the stomachs are removed and examined for ulceration. Ulcers are graded on a 0–4 scale and the number of ulcers is recorded. Pretreatment with the 1,5-disubstituted biguanide compounds of this invention produces a decrease in ulcer grade and the number of ulcers compared to the control reserpine-treated rats.

Determination of anti-spasmodic properties can be carried out by the procedure as outlined by D. A. Brodie and S. K. Kundrats in their article entitled "Effect of Drugs on Gastric Emptying in Rats", *Fed. Proc.* 24:714 (1965).

The biguanides of this invention have also been found to be mucogenic agents, that is, they increase the biosynthesis of mucopolysaccharides of the gastric mucous membrane which is a mechanism for inhibiting gastro-intestinal ulcer. This property is determined by the test outlined in the *J. Pharm. Pharmac.*, 1970, 22, 143–4.

Mydriasis is detected by the procedure R. A. Turner, *Screening Methods in Pharmacology*, Academic Press, New York, and London, pp. 174–5, 1965. Acute toxicity is calculated according to the standard Litchfield-Wilcoxon procedure.

In view of the results of these tests, the pharmacological data clearly indicates that the 1-aryl and aralkyl-5-substituted biguanides of this invention can be considered to be effective anti-ulcerogenic agents having active gastric anti-secretory and anti-spasmodic properties which are substantially free of anti-cholinergic side effects and having a low toxicity.

The following are detailed examples which show the preparation of the compounds of this invention. They are to be construed as illustrations of said compounds and not as limitations thereof.

EXAMPLE 1

1-(p-Trifluoromethoxyphenyl)-5-i-propylbiguanide dihydrochloride

A stirred mixture of 6.3 g. (0.0296 mole) of p-aminophenyltrifluoromethyl ether hydrochloride and 3.78 g. (0.0296 mole) of 1-i-propyl-3-cyanoguanidine is immersed in a 210°C. oil bath for fifteen minutes. The resulting reaction product is dissolved in 100 ml of water, alkalized with 40% sodium hydroxide solution, and extracted with 250 ml of ether. The ether layer is backwashed twice with 10 ml of water, dried over sodium carbonate, filtered, and the ether solution made strongly acidic with a saturated ethereal hydrochloric acid solution. The precipitate is collected on a filter, washed twice with 50 ml of anhydrous ether, and dried at 25°C/125 mm. Recrystallization from a mixture of isopropanol and cyclohexane (1:1) gives 1-(p-trifluoromethoxyphenyl)-5-i-propylbiguanide dihydrochloride.

EXAMPLE 2

1-(p-Trifluoromethylbenzyl)-5-i-propylbiguanide dihydrochloride

A stirred mixture of 6.9 g (0.035 mole) of p-trifluoromethylbenzylamine hydrochloride and 4.3 (0.035 mole) of 1-i-propyl-3-cyanoguanidine is immersed in a 180°C oil bath for 1 hour. The melt is cooled and dissolved in 35 ml of hot water. The solution is cooled in an ice bath, made alkaline with 40% sodium hydroxide solution, and extracted with 150 ml of ether. The ether layer is dried over potassium carbonate, filtered and the ether solution made strongly acidic with a saturated ethereal hydrochloric acid solution. The precipitate is washed twice with 25 ml of anhydrous ether and recrystallized from a mixture of ethanol and heptane (3:5) to obtain 1-(p-trifluoromethylbenzyl)-5-i-propylbiguanide dihydrochloride.

EXAMPLE 3

1-($\alpha$-Methyl-p-trifluoromethylbenzyl)-5-i-propylbiguanide dihydrochloride

A stirred mixture of 15.5 g (0.0687 mole) of $\alpha$-methyl-p-trifluoromethylbenzylamine hydrochloride and 9.55 g (0.0756 mole) of 1-i-propyl-3-cyanoguanidine is immersed in a 190°C oil bath for ten minutes. The melt is cooled to room temperature, dissolved in 100 ml of water, made alkaline with 40% sodium hydroxide solution and extracted twice with 200 ml of ether. The combined ether extracts are dried over potassium carbonate, filtered, and the ether solution made strongly acidic with a saturated ethereal hydrochloric acid ether solution. The precipitate is collected on a filter, washed twice with 50 ml of anhydrous ether, and dried at 40°C/125 mm. for 5 hours. The dihydrochloride is dissolved in 50 ml of water, made strongly alkaline with 40% sodium hydroxide solution, and extracted twice with 100 ml of ether. The combined ether extracts are dried over potassium carbonate, filtered, and the ether solution made strongly acidic with a saturated ethereal hydrochloric acid solution. The precipitate is collected on a filter, washed twice with 50 ml of anhydrous ether, and dried at 40°C/125 mm. to obtain 1-($\alpha$-methyl-p-trifluoromethylbenzyl)-5-i-propylbiguanide dihydrochloride.

EXAMPLE 4

1-(p-Trifluoromethylphenyl)-5-i-propylbiguanide hydrochloride

A mixture of 8.7 g (0.69 mole) of 1-i-propyl-3-cyanoguanidine, 11.15 g (0.069 mole) of p-amino-benzotrifluoride and 23 ml of 3NHcl is heated at 50°C with stirring for 16 hours. The reaction mixture is then cooled in an ice bath, made strongly alkaline with 35 ml of 2.5 N sodium hydroxide and extracted into 700 ml of ether. The ether extract is worked with 2–25 ml portions of 5 N sodium hydroxide and then dried over potassium carbonate. The ether solution is evaporated to a viscous oil dissolved in methanol and the pH adjusted to 7.0 with 5 N methanolic HCl. The mixture is evaporated to a slurry and then enough methanol added to reach solution. This is followed by the addition of 1 liter of ether to precipitate the monohydrochloride. The solid is filtered off and dried at 50°C/128mm to obtain 1-(p-trifluoromethylphenyl)-5-i-propylbiguanide hydrochloride.

EXAMPLE 5

1-(p-N,N-Dimethylsulfamylphenyl)-5-i-propylbiguanide

To 11 g (0.055 mole) of p-N,N-dimethylsulfamylaniline is added 17.68 ml (0.055) of 3.1 N hydrochloric acid. This is heated on a steam bath with 15 ml of isopropanol and 6.94 g (0.055 mole) of 1-i-propyl-3-cyanoguanidine. The reaction mixture is heated for 18 hours. The alcohol is evaporated off and diluted with 250 ml of 7.4% hydrochloric acid. The mixture is filtered, cooled and made alkaline with 10% sodium hydroxide. The precipitate is filtered, triturated with 100 ml of boiling isopropanol and filtered to get 1-(p-N,N-dimethylsulfamylphenyl)-5-i-propylbiguanide.

EXAMPLE 6

1-[3,5-Di(trifluoromethyl)phenyl]-5-methylbiguanide

To 22.9 g (0.1 mole) of 3,5-di(trifluoromethyl)aniline and 12.6 g (0.1 mole) of 1-methyl-3-cyanoguanidine is added 10 ml of concentrated hydrochloric acid and 20 ml of water. The solution is heated on a steam bath for 1 hour at which time a solid precipitates out. The reaction mixture is cooled to room temperature, made strongly alkaline with 40% NaOH and extracted with ether. The ether layer is dried over potassium carbonate, and evaporated in vacuo to obtain an oil. The residue is triturated with 500 ml heptane and the solid which forms is recrystallized from methylene chloride to obtain 1-[3,5-di(fluoromethyl)phenyl]-5-methylbiguanide.

EXAMPLE 7

1-(2,3,4,5,6-Pentafluorophenyl)-5-cyclopropylbiguanide

A mixture of 7.0 g (0.035 mole) of 2,3,4,5,6-pentafluoroaniline hydrochloride and 4.4 g (0.035 mole) of 1-cyclopropyl-3-cyanoguanidine is heated at a melt for 1½ hours. The mixture is then cooled, heated with 25 ml of water until solution and then made alkaline with 40% sodium hydroxide. The solution is extracted with ether and dried over potassium carbonate and evaporated to dryness. The residue is chromatogramed on silica gel using isopropanol:NH$_4$OH to obtain 1-(2,3,4,5,6-pentafluorophenyl)-5-cyclopropylbiguanide.

EXAMPLE 8

1-(2,4,6-Trichlorophenyl)-5-methylbiguanide hydrochloride

To 20 g (0.1 mole) of 2,4,6-trichloroaniline and 12.6 g (0.1 mole) of 1-methyl-3-cyanoguanidine in 10 ml (0.1 mole) of concentrated hydrochloric acid is added 125 ml of n-butanol. The reaction mixture is refluxed for 17 hours, cooled and the alcohol evaporated off. The residue is extracted with ether after making it alkaline with 40% sodium hydroxide. The ether extract is dried over potassium carbonate and evaporated. The residue is dissolved in methanol, the pH adjusted to about 7, charcoal filtered and evaporated. The residue is triturated with ether and the solid that forms is recrystallized from water to obtain 1-(2,4,6-trichlorophenyl)-5-methylbiguanide hydrochloride.

EXAMPLE 9

When the procedure of Example 8 is followed but the starting material is substituted for those below, then the corresponding product is obtained.

| Starting Material | Product |
| --- | --- |
| 2,6-dibromoaniline | 1-(2,6-dibromophenyl)-5-methylbiguanide |
| 2,3,4-trichloroaniline | 1-(2,3,4-trichlorophenyl)-5-methylbiguanide |
| 2,3,5-trichloroaniline | 1-(2,3,5-trichlorophenyl)-5-methylbiguanide |
| 2,6-dichloro-4-nitroaniline | 1-(2,6-dichloro-4-nitrophenyl)-5-methylbiguanide |
| 2,6-dimethoxyaniline | 1-(2,6-dimethoxyphenyl)-5-methylbiguanide |
| 2,6-dichloro-4-(p-chlorophenyl) aniline | 1-[2,6-dichloro-4-(p-chlorophenyl) phenyl]-5-methylbiguanide |
| 2,6-dichloro-4-dimethylsulfamido-aniline | 1-(2,6-dichloro-4-dimethylsulfamido-phenyl)-5-methylbiguanide |
| 2,6-difluoroaniline | 1-(2,6-difluorophenyl)-5-methylbiguanide |
| 2,6-dichlorobenzylamine | 1-(2,6-dichlorobenzyl)-5-methylbiguanide |
| 2,6-dibromobenzylamine | 1-(2,6-dibromobenzyl)-5-methylbiguanide |
| 2,4,6-trichlorobenzylamine | 1-(2,4,6-trichlorobenzyl)-5-methylbiguanide |
| 2,6-dichloro-α-methylbenzylamine | 1-(2,6-dichloro-α-methylbenzyl)-5-methylbiguanide |
| 2,4,6-trichloro-α-methylbenzyl-amine | 1-(2,4,6-trichloro-α-methylbenzyl)-5-methylbiguanide |
| 2,6-dinitroaniline | 1-(2,6-dinitrophenyl)-5-methylbiguanide |
| 3,4,5-trimethoxyaniline | 1-(3,4,5-trimethoxyphenyl)-5-methylbiguanide |
| 2,4,6-trimethoxyaniline | 1-(2,4,6-trimethoxyphenyl)-5-methylbiguanide |
| 3,5-dichloro-4-methoxyaniline | 1-(3,5-dichloro-4-methoxyphenyl)-5-methylbiguanide |

-continued

| Starting Material | Product |
| --- | --- |
| 2,3,4,5-tetrafluoroaniline | 1-(2,3,4,5-tetrafluorophenyl)-5-methyl-biguanide |
| 2,6-difluorobenzylamine | 1-(2,6-difluorobenzyl)-5-methyl-biguanide |
| 2,6-dibromo-α-methylbenzylamine | 1-(2,6-dibromo-α-methylbenzyl)-5-methylbiguanide |
| 2,6-dichloro-4-hydroxyaniline | 1-(2,6-dichloro-4-hydroxyphenyl)-5-methylbiguanide |
| 2,4,6-tribromobenzylamine | 1-(2,4,6-tribromobenzyl)-5-methyl-biguanide |
| 2,6-dichloro-4-carboxyaniline | 1-(2,6-dichloro-4-carboxyphenyl)-5-methylbiguanide |
| 4-phenylaniline | 1-(4-biphenylyl)-5-methylbiguanide |
| 2,6-dichloro-4-carbethoxyaniline | 1-(2,6-dichloro-4-carbethoxyphenyl)-5-methylbiguanide |
| 2,6-dicarbethoxyaniline | 1-(2,6-dicarbethoxyphenyl)-5-methyl-biguanide |
| 4-acetoxybenzylamine | 1-(4-acetoxybenzyl)-5-methylbiguanide |
| o,m & p-trifluoromethoxybenzylamine | 1-(o,m & p-trifluoromethoxybenzyl)-5-methylbiguanide |
| 4-(p-chlorophenoxy)aniline | 1-[4-(p-chlorophenoxy)phenyl]-5-methylbiguanide |
| 2,6-dichloro-4-dimethylaminoaniline | 1-(2,6-dichloro-4-dimethylamino-phenyl)-5-methylbiguanide |
| p-cyanobenzylamine | 1-(p-cyanobenzyl)-5-methylbiguanide |
| 2,6-di(trifluoromethyl)aniline | 1-[2,6-di(trifluoromethyl)phenyl]-5-methylbiguanide |
| p-fluoro-α-methylbenzylamine | 1-(p-fluoro-α-methylbenzyl)-5-methyl-biguanide |
| 2,6-dichloro-α,α-dimethylbenzylamine | 1-(2,6-dichloro-α,α-dimethylbenzyl)-5-methylbiguanide |
| p-chloro-α-methylbenzylamine | 1-(p-chloro-α-methylbenzyl)-5-methyl-biguanide |
| o & m-trifluoromethyl-α-methyl-benzylamine | 1-(o & m-trifluoromethyl-α-methyl-benzyl)-5-methylbiguanide |
| 2,6-di-i-propylaniline | 1-(2,6-di-i-propylphenyl)-5-methyl-biguanide |
| 2,4-dichloroaniline | 1-(2,4-dichlorophenyl)-5-methyl-biguanide |
| 2,4-dibromoaniline | 1-(2,4-dibromophenyl)-5-methylbiguanide |
| 2,4-difluoroaniline | 1-(2,4-difluorophenyl)-5-methyl-biguanide |
| 2,3-difluoroaniline | 1-(2,3-difluorophenyl)-5-methyl-biguanide |
| 2,5-difluoroaniline | 1-(2,5-difluorophenyl)-5-methyl-biguanide |
| p-fluoroaniline | 1-(p-fluorophenyl)-5-methylbiguanide |
| p-chloroaniline | 1-(p-chlorophenyl)-5-methylbiguanide |
| p-bromoaniline | 1-(p-bromophenyl)-5-methylbiguanide |
| p-iodoaniline | 1-(p-iodophenyl)-5-methylbiguanide |

EXAMPLE 10

1-(2,6-Dibromo-4-trifluoromethylphenyl)-5-methyl-biguanide

To a slurry of 15 g (0.06 mole) of 1-(p-trifluoromethylphenyl)-5-methylbiguanide in 200 ml of water is added dropwise 10.2 g (0.12 mole) of bromine over a period of 3 hours. The reaction mixture is cooled and the unreacted bromine discharged with sodium bisulfite. The mixture is made strongly alkaline and extracted into ether. The ether layer is dried over Na$_2$SO$_4$, charcoaled filtered and evaporated. The solid residue is recrystallized from dioxane/water to obtain 1-(2,6-dibromo-4-trifluoromethylphenyl)-5-methylbiguanide.

When the procedure of Example 10 is followed but the starting material is substituted for those below, then the corresponding product is obtained.

| Starting Material | Product |
| --- | --- |
| 1-(4-bromophenyl)-5-i-propyl biguanide | 1-(2,4,6-tribromophenyl)-5-i-propylbiguanide |
| 1-(4-fluorophenyl)-5-methyl-biguanide | 1-(2,6-dibromo-4-fluorophenyl)-5-methylbiguanide |
| 1-(4-chlorophenyl)-5-methyl-biguanide | 1-(2,6-dibromo-4-chlorophenyl)-5-methylbiguanide |
| 1-(2,6-dichlorophenyl)-5-methylbiguanide | 1-(2,6-dichloro-4-bromophenyl)-5-methylbiguanide |
| 1-(4-iodophenyl)-5-methyl-biguanide | 1-(2,6-dibromo-4-iodophenyl)-5-methylbiguanide |
| 1-(4-nitrophenyl)-5-methyl-biguanide | 1-(2,6-dibromo-4-nitrophenyl)-5-methylbiguanide |
| 1-(4'-chloro-4-biphenyl)-5-methylbiguanide | 1-(2,6-dibromo-4'-chloro-4-biphenyl)-5-methylbiguanide |
| 1-(4-phenoxyphenyl)-5-methyl biguanide | 1-(2,6-dibromo-4-phenoxyphenyl)-5-methylbiguanide |
| 1-[4-(4'-chlorophenoxy)phenyl]-5-methylbiguanide | 1-[2,6-dibromo-4-(4'-chlorophenoxy)phenyl]-5-methylbiguanide |
| 1-(2,4-dichlorophenyl)-5-methyl biguanide | 1-(2,4-dichloro-6-bromophenyl)-5-methylbiguanide |

When chlorine is used in the above example, then the corresponding chlorinated product is obtained.

EXAMPLE 11

1-(2,6-Dichloro-4-thiocyanatophenyl)-5-methylbiguanide

A solution of 1-(2,6-dichlorophenyl)-5-methylbiguanide (28.0 g) (0.1 mole) in methanol (60 ml) previously saturated with sodium bromide is cooled to 5°C with stirring. Sodium thiocyanate is added and stirring continued for 10 minutes.

To this mixture is added dropwise with stirring, a solution of bromine (17.6 g) in methanol (20 ml) previously saturated with sodium bromide. When reaction is complete, water is added (300 ml) and the mixture made alkaline (pH12) with 40% sodium hydroxide. The organic base is extracted into ether, and the ether solution washed with brine, dried ($Na_2SO_4$) and evaporated to dryness. The residue is crystallized from aqueous methanol to give 1-(2,6-dichloro-4-thiocyanatophenyl)-5-methylbiguanide.

When the procedure of Example 11 is followed but the starting material is substituted for these below, then the corresponding product is obtained.

| Starting Material | Product |
|---|---|
| 1-(2,6-dibromopheny)-5-methyl-biguanide | 1-(2,6-dibromo-4-thiocyanatophenyl)-5-methylbiguanide |
| 1-(2,4-dichlorophenyl)-5-methyl biguanide | 1-(2,4-dichloro-6-thiocyanatophenyl)-5-methylbiguanide |
| 1-(2-chlorophenyl)-5-methyl biguanide | 1-(2-chloro-4,6-dithiocyanatophenyl)-5-methylbiguanide |
| 1-(2,4-dibromophenyl)-5-methyl biguanide | 1-(2,4-dibromo-6-thiocyanatophenyl)-5-methylbiguanide |

EXAMPLE 12

1-(4-Nitro-2,6-dichlorophenyl)-5-methylbiguanide 1-(2,6-Dichlorophenyl)-5-methylbiguanide hydrochloride (14 g) is added to concentrated sulfuric acid (18 ml) and stirred for 5 minutes. Concentrated nitric acid (Sp. G. 1.51) (2.5 ml) is added dropwise, maintaining the temperature between 30° and 40° by water cooling if necessary. After addition of the nitric acid is complete, the mixture is stirred for 10 minutes, then poured into water. The mixture is made alkaline with sodium hydroxide, then extracted with ether. The ether extract is washed, dried ($Na_2SO_4$), evaporated and the residue crystallized from aqueous methanol to give 1-(4-nitro-2,6-dichlorophenyl)-5-methylbiguanide.

When the procedure of Example 12 is followed but the starting material is substituted for those below, then the corresponding product is obtained.

| Starting Material | Product |
|---|---|
| 1-(4-trifluoromethylphenyl)-5-methylbiguanide | 1-(2,6-dinitro-4-trifluoromethylphenyl)-5-methylbiguanide |
| 1-(4-bromophenyl)-5-methyl biguanide | 1-(2,6-dinitro-4-bromophenyl)-5-methylbiguanide |
| 1-(2-iodophenyl)-5-methyl biguanide | 1-(2-iodo-4,6-dinitrophenyl)-5-methylbiguanide |
| 1-(4-chlorophenyl)-5-methyl biguanide | 1-(2,6-dinitro-4-chlorophenyl)-5-methylbiguanide |
| 1-(4-iodophenyl)-5-methylbiguanide | 1-(2,6-dinitro-4-iodophenyl)-5-methylbiguanide |
| 1-(2,4-dichlorophenyl)-5-methyl biguanide | 1-(2,4-dichloro-6-nitrophenyl)-5-methylbiguanide |
| 1-(2,4-dibromophenyl)-5-methyl-biguanide | 1-(2,4-dibromo-6-nitrophenyl)-5-methylbiguanide |
| 1-(2-chlorophenyl)-5-methyl-biguanide | 1-(2-chloro-4,6-dinitrophenyl)-5-methylbiguanide |
| 1-(2-iodophenyl)-5-methylbiguanide | 1-(2-iodo-4,6-dinitrophenyl)-5-methylbiguanide |
| 1-[4-(p-chlorophenoxy)phenyl]-5-methylbiguanide | 1-[2,6-dinitro-4-(p-chlorophenoxy)phenyl]-5-methylbiguanide |
| 1-(2,6-dichloro-α-methylbenzyl)-5-methylbiguanide | 1-(2,6-dichloro-4-nitro-α-methylbenzyl)-5-methylbiguanide |
| 1-(2,6-dibromophenyl)-5-methyl-biguanide | 1-(2,6-dibromo-4-nitrophenyl)-5-methylbiguanide |
| 1-[4-(p-chlorophenyl)phenyl]-5-methylbiguanide | 1-[2,6-dinitro-4-(p-chlorophenyl)phenyl]-5-methylbiguanide |

EXAMPLE 13

1-(2,6-Dibromophenyl)-5-methylbiguanide hydroiodide

A solution of 1-(2,6-dibromo-4-iodophenyl)-5-methylbiguanide (47 g) (0.1 mole) in methanol (500 ml) is shaken in an atmosphere of hydrogen in the presence of 5% palladium on charcoal (1 g). When the hydrogen uptake is measured to be 2.4 liter at room temperature and pressure, the shaking is stopped and the mixture filtered through diatomaceous earth.

The filtrate is evaporated to dryness and the solid residue dissolved in methanol (100 ml). Upon addition of ether (150 ml) with stirring, 1-(2,6-dibromophenyl)-5-methylbiguanide hydroiodide is obtained.

EXAMPLE 14

1-(p-Trifluoromethylphenyl)-5-cyclopropylbiguanide hydrochloride

A stirred mixture of 16.1 g (0.1 mole) of p-trifluoromethylaniline, 12.6 g (0.1 mole) of 1-cyclopropyl-3-cyanoguanidine and 385 ml of 2.6 N hydrochloric acid (0.1 mole) is treated at 60°C for several hours. The reaction mixture is then cooled, alkylated with 40% sodium hydroxide and extracted with 1:1 etherethanol. The extract is washed with a saturated saline solution and dried over sodium sulfate. The solvent is evaporated and replaced with benzene which on concentrating results in the crude product. The residue is dissolved in 100 ml of hot methanol and 200 ml of water is added. The precipitate is removed, washed with water and dried. The hydrochloride salt is then formed in alcohol to obtain 1-(p-trifluoromethylphenyl)-5-cyclopropylbiguanide hydrochloride.

When an equimolar amount of the cyanoguanidine compounds of Table 1 below are used in the above example in place of 1-cyclopropyl-3-cyanoguanidine then the corresponding product of Table II below is prepared.

TABLE I 1,1-dimethyl-3-cyanoguanidine
1,1-di-i-propyl-3-cyanoguanidine
1-methyl-1-ethyl-3-cyanoguanidine
1-propyl-1-ethyl-3-cyanoguanidine
1-methyl-3-cyanoguanidine
1-heptyl-3-cyanoguanidine
1-octyl-3-cyanoguanidine
1,1-dioctyl-3-cyanoguanidine
1-nonyl-3-cyanoguanidine
1-methallyl-3-cyanoguanidine
1-(2-pentenyl)-3-cyanoguanidine
1,1-di-cyclopropyl-3-cyanoguanidine
1-cyclobutyl-3-cyanoguanidine
1-t-butyl-3-cyanoguanidine
1-cyclohexyl-3-cyanoguanidine
1,1-di-cyclohexyl-3-cyanoguanidine
1-(cyclohexen-2-yl)-3-cyanoguanidine
1-cyclooctyl-3-cyanoguanidine
1-cyclopropylmethyl-3-cyanoguanidine
1-phenyl-3-cyanoguanidine
1-benzyl-3-cyanoguanidine
1-phenethyl-3-cyanoguanidine
1-(cyclohexen-2-ylmethyl-3-cyanoguanidine
N-(N-cyanoamidino)piperdine
N-(N-cyanoamidino)morpholine
N-(N-cyanoamidino)-2-thiazolidine
N-(N-cyanoamidino)-4-methylpiperazine
N-(N-cyanoamidino)octamethyleneamine

TABLE II 1-(p-trifluoromethylphenyl)-5,5-dimethylbiguanide
1-(p-trifluoromethylphenyl)-5,5-di-i-propylbiguanide
1-(p-trifluoromethylphenyl)-5-methyl-5-ethylbiguanide
1-(p-trifluoromethylphenyl)-5-propyl-5-ethylbiguanide
1-(p-trifluoromethylphenyl)-5-methylbiguanide
1-(p-trifluoromethylphenyl)-5-heptylbiguanide
1-(p-trifluoromethylphenyl)-5-octylbiguanide
1-(p-trifluoromethylphenyl)-5,5-dioctylbiguanide
1-(p-trifluoromethylphenyl)-5-nonylbiguanide
1-(p-trifluoromethylphenyl)-5-methallylbiguanide
1-(p-trifluoromethylphenyl)-5-(2-pentenyl)biguanide
1-(p-trifluoromethylphenyl)-5,5-di-cyclopropylbiguanide
1-(p-trifluoromethylphenyl)-5-cyclobutylbiguanide
1-(p-trifluoromethylphenyl)-5-t-butylbiguanide
1-(p-trifluoromethylphenyl)-5-cyclohexylbiguanide
1-(p-trifluoromethylphenyl)-5,5-dicyclohexylbiguanide
1-(p-trifluoromethylphenyl)-5-(cyclohexen-2-yl)biguanide
1-(p-trifluoromethylphenyl)-5-(cyclohexen-2-ylmethyl)biguanide
1-(p-trifluoromethylphenyl)-5-cyclooctylbiguanide
1-(p-trifluoromethylphenyl)-5-cyclopropylmethylbiguanide
1-(p-trifluoromethylphenyl)-5-phenylbiguanide
1-(p-trifluoromethylphenyl)-5-benzylbiguanide
1-(p-trifluoromethylphenyl)-5-phenethylbiguanide
1-(p-trifluoromethylphenyl)-5,5-pentamethylenebiguanide
1-(p-trifluoromethylphenyl)-5,5-diethyleneoxybiguanide
1-(p-trifluoromethylphenyl)-5,5-trimethylenethiobiguanide
1-(p-trifluoromethylphenyl)-5,5-ethylenemethyliminotrimethylene biguanide
1-(p-trifluoromethylphenyl)-5,5-octamethylenebiguanide

EXAMPLE 15

When an equimolar amount of the cyanoguanidine compounds of Example 14 are combined with the aniline compounds of Examples 1–9, then the following representative compounds are prepared.

1-(p-trifluoromethoxyphenyl)-5-cyclopropylbiguanide
1-(α-methyl-p-trifluoromethylbenzyl)-5-cyclopropylbiguanide
1-(2,4,6-trichlorophenyl)-5-cyclopropylbiguanide
1-(2,3,4,5,6-pentafluorophenyl)-5-cyclopropylbiguanide
1-(2,6-dichlorophenyl)-5-cyclopropylbiguanide
1-(2,6-dichlorophenyl)-5-benzylbiguanide
1-(2,6-dibromophenyl)-5,5-di-i-propylbiguanide
1-[2,6-dichloro-4-(p-chlorophenyl)phenyl]-5-octylbiguanide
1-(4-biphenyl)-5-cyclohexylbiguanide
1-(4-acetoxyphenyl)-5-phenylbiguanide
1-(2,6-dichloro-α,α-dimethylbenzyl)-5-phenethylbiguanide
1-(2,6-dichlorophenyl)-5,5-pentamethylenebiguanide
1-(p-cyanophenyl)-5-nonylbiguanide
1-(2,6-dibromophenyl)-5-cyclopropylmethylbiguanide
1-(p-chlorophenoxyphenyl)-5-methallylbiguanide
1-(2,6-dichloro-4-dimethylamino)phenyl-5-(2-pentenyl)biguanide
1-(2,6-dibromo-4-fluorophenyl)-5,5-di-octylbiguanide
1-(2,6-dibromophenyl)-5,5-diethyleneoxybiguanide
1-(2,6-dichloro-4-carboxyphenyl)-5-cyclopropylbiguanide 1-(2,6-dichloro-4-hydroxyphenyl)-5-cyclopropylbiguanide
1-(3,5-dichloro-4-methoxyphenyl)-5-cyclohexylbiguanide
1-(2,6-dichloro-4-nitrophenyl)-5,5-dimethylbiguanide
1-(2,6-dichloro-4-dimethylsulfamidophenyl)-5-cyclobutyl biguanide
1-(p-fluoro-α-methylbenzyl)-5-methyl-5-ethylbiguanide
1-(p-fluorophenyl)-5,5-di-cyclohexylbiguanide
1-(4-phenoxyphenyl)-5-t-butylbiguanide
1-(2,4-difluorophenyl)-5,5-di-cyclopropylbiguanide
1-(2,3-difluorophenyl)-5-cyclohexylbiguanide
1-(2,5-difluorophenyl)-5-t-butylbiguanide
1-(2,6-di-i-propylphenyl)-5-i-propylbiguanide
1-(p-fluorophenyl)-5-octylbiguanide
1-(p-fluorophenyl)-5-cyclopropylmethylbiguanide

EXAMPLE 16

Following the procedure of Example 4 but substituting the following trifluoromethylaniline compounds and 1-methyl-3-cyanoguanidine, then the following products are prepared.

| | |
|---|---|
| 2-amino-5-nitrobenzotrifluoride | 1-(4-nitro-2-trifluoromethylphenyl)-5-methylbiguanide |
| 2-nitro-4-aminobenzotrifluoride | 1-(3-nitro-4-trifluoromethylphenyl)-5-methylbiguanide |
| 3-nitro-4-aminobenzotrifluoride | 1-(2-nitro-4-trifluoromethylphenyl)-5-methylbiguanide |
| 2-amino-5-fluorobenzotrifluoride | 1-(4-fluoro-2-trifluoromethylphenyl)-5-methylbiguanide |
| 2-fluoro-5-aminobenzotrifluoride | 1-(4-fluoro-3-trifluoromethylphenyl)-5-methylbiguanide |
| 3-amino-4-fluorobenzotrifluoride | 1-(2-fluoro-5-trifluoromethylphenyl)-5-methylbiguanide |
| 3-amino-4-bromobenzotrifluoride | 1-(2-bromo-5-trifluoromethylphenyl)-5-methylbiguanide |
| 3-amino-4-chlorobenzotrifluoride | 1-(2-chloro-5-trifluoromethylphenyl)-5-methylbiguanide |
| 2-chloro-5-aminobenzotrifluoride | 1-(4-chloro-3-trifluoromethylphenyl)-5-methylbiguanide |
| 2-bromo-5-aminobenzotrifluoride | 1-(4-bromo-3-trifluoromethylphenyl)-5-methylbiguanide |
| 2-amino-5-bromobenzotrifluoride | 1-(4-bromo-2-trifluoromethylphenyl)-5-methylbiguanide |

6. 1-(p-trifluoromethylphenyl)-5-cyclopropylmethylbiguanide.
7. 1-(p-trifluoromethylphenyl)-5-cyclopropylbiguanide.
8. 1-(p-trifluoromethylphenyl)-5-i-propylbiguanide.
9. 1-(2,6-dichloro-4-trifluoromethylphenyl)-5-i-propylbiguanide.
10. 1-(p-trifluoromethylphenyl)-5-octylbiguanide.
11. 1-(4-nitro-2-trifluoromethylphenyl)-5-methylbiguanide.
12. 1-(3-nitro-4-trifluoromethylphenyl)-5-methylbiguanide.
13. 1-(2-nitro-4-trifluoromethylphenyl)-5-methylbiguanide.
14. 1-(4-fluoro-2-trifluoromethylphenyl)-5-methylbiguanide.
15. 1-(4-fluoro-3-trifluoromethylphenyl)-5-methylbiguanide.
16. 1-(2-fluoro-5-trifluoromethylphenyl)-5-methylbiguanide.
17. 1-(2-bromo-5-trifluoromethylphenyl)-5-methylbiguanide.
18. 1-(2-chloro-5-trifluoromethylphenyl)-5-methylbiguanide.

We claim:
1. 1-(p-trifluoromethoxyphenyl)-5-i-propylbiguanide.
2. 1-(p-trifluoromethylphenyl)-5-benzylbiguanide.
3. 1-(p-trifluoromethylphenyl)-5-methallylbiguanide.
4. 1-(p-trifluoromethylphenyl)-5,5-pentamethylenebiguanide.
5. 1-(p-trifluoromethylphenyl)-5-phenylbiguanide.
19. 1-(3-trifluoromethyl-4-chlorophenyl)-5-methylbiguanide.
20. 1-(3-trifluoro-4-bromophenyl)-5-methylbiguanide.
21. 1-(2-trifluoromethyl-4-bromophenyl)-5-methylbiguanide.

* * * * *